United States Patent
Cohen et al.

(10) Patent No.: US 9,005,219 B2
(45) Date of Patent: Apr. 14, 2015

(54) MULTIFUNCTIONAL CORE FOR TWO-PIECE HEMOSTASIS CLIP

(75) Inventors: Adam L. Cohen, Arlington, MA (US); Benjamin E. Morris, Jeffersonville, IN (US); John Miser, Crestwood, KY (US); Gregory R. Furnish, Louisville, KY (US); Gary A. Jordan, Litchfield, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 786 days.

(21) Appl. No.: 12/853,478

(22) Filed: Aug. 10, 2010

(65) Prior Publication Data
US 2011/0046651 A1 Feb. 24, 2011

Related U.S. Application Data

(60) Provisional application No. 61/235,105, filed on Aug. 19, 2009.

(51) Int. Cl.
*A61B 17/10* (2006.01)
*A61B 17/122* (2006.01)
*A61B 17/128* (2006.01)
*A61B 17/00* (2006.01)

(52) U.S. Cl.
CPC ......... *A61B 17/1227* (2013.01); *A61B 17/1285* (2013.01); *A61B 2017/00473* (2013.01)

(58) Field of Classification Search
USPC .......................... 606/139, 142, 143, 151, 157
See application file for complete search history.

(56) References Cited

U.S. PATENT DOCUMENTS 8,070,760 B2 12/2011 Fujita
2005/0080440 A1 4/2005 Durgin et al.

FOREIGN PATENT DOCUMENTS

EP 1 829 489 9/2007

*Primary Examiner* — Dianne Dornbusch
(74) *Attorney, Agent, or Firm* — Fay Kaplun & Marcin, LLP

(57) ABSTRACT

A device includes a clip including first and second arms distal ends of which are biased apart and a core member including first and second portions connected to one another via a frangible link. The first portion includes a first protrusion for engaging a cut-out in the first arm. The frangible link is fractured when subjected to a load of at least a predetermined level deploying the clip. The device also includes a capsule slidably housing the core member and a proximal portion of the clip.

22 Claims, 21 Drawing Sheets

MULTIFUNCTIONAL CORE FOR TWO-PIECE HEMOSTASIS CLIP

PRIORITY CLAIM

This application claims the priority to the U.S. Provisional Application Ser. No. 61/235,105, entitled "Multifunctional Core for Two-Piece Hemostasis Clip," filed on Aug. 19, 2009. The specification of the above-identified application is incorporated herewith by reference.

BACKGROUND

Many pathologies of the gastrointestinal ("GI") system, the biliary tree, the vascular system and other body lumens and hollow organs are treated through endoscopic procedures, many of which require active and/or prophylactic hemostasis to control internal bleeding. Tools for deploying hemostatic clips via endoscopes are often used to stop internal bleeding by clamping together the edges of wounds or incisions. Hemostasis clips grasp tissue surrounding a wound and hold edges of the wound together to allow natural healing processes to close the wound. Specialized endoscopic clipping devices are used to deliver the clips to desired locations within the body and to position and deploy the clips at the desired locations within the body after which the clip delivery device is withdrawn, leaving the clip within the body.

One and two piece hemostatic clip structures are currently known in the art. Although one piece clips may be delivered to desired locations using a single stage deployment concept, two piece clip designs generally require a two stage deployment process.

SUMMARY OF THE INVENTION

The present invention is directed to a device, comprising a clip including first and second arms distal ends of which are biased apart and a core member including first and second portions connected to one another via a frangible link, the first portion including a first protrusion for engaging a cut-out in the first arm, wherein the frangible link is fractured when subjected to a load of at least a predetermined level deploying the clip in combination with a capsule slidably housing the core member and a proximal portion of the clip.

DETAILED DESCRIPTION

Figure 1:
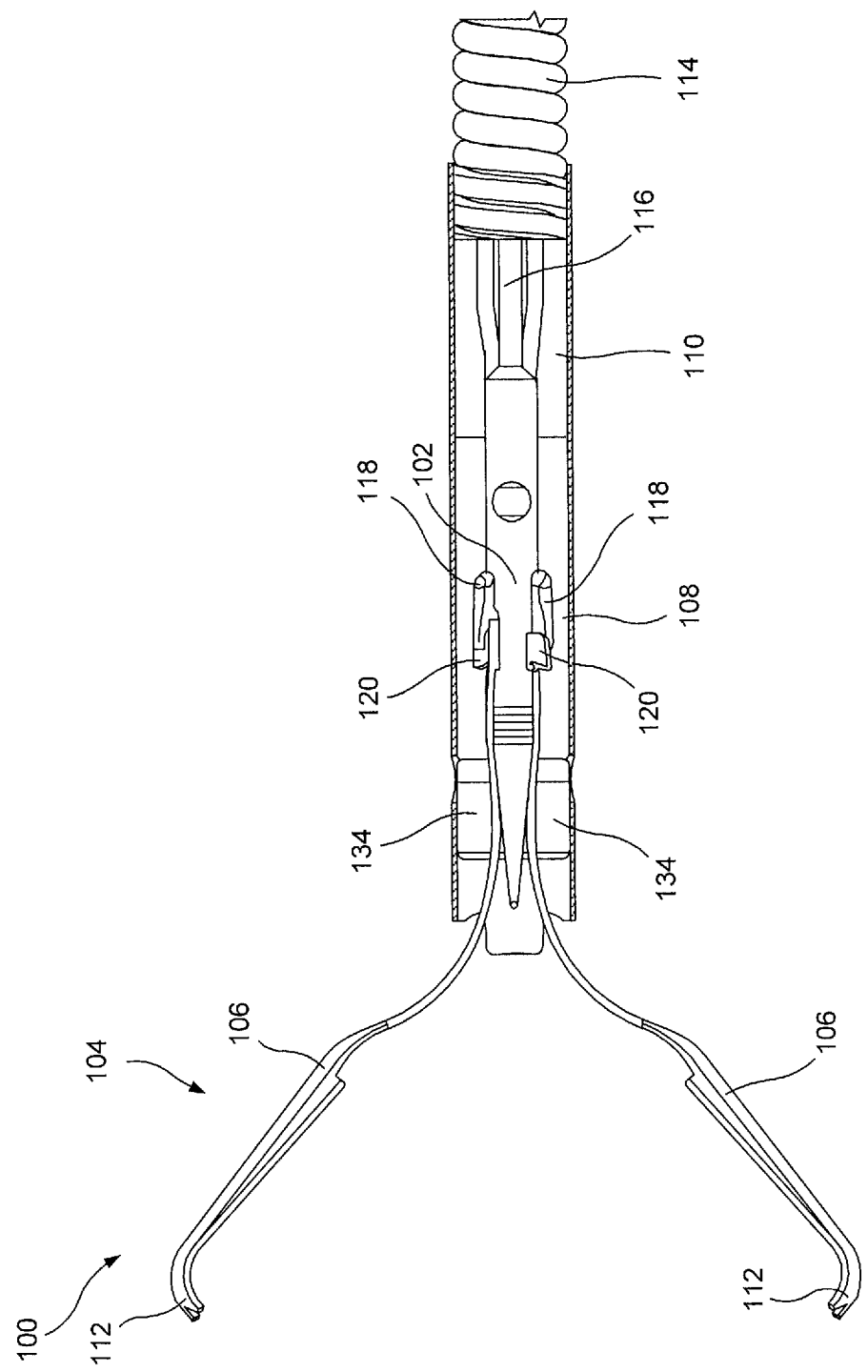
FIG. 1 shows a side view of a device according to a first exemplary embodiment of the invention.

The present invention may be further understood with reference to the following description and the appended drawings, wherein like elements are referred to with the same reference numerals. The present invention relates to devices for hemostatic clipping, and in particular, to a hemostatic clip that may be deployed in a single stage deployment process. Exemplary embodiments of the present invention provide a two-piece hemostatic clip including a multifunctional core member, which allows the clip to be properly oriented and repeatedly opened/closed while controlling stress areas such that the clip may deployed in the single stage process. These embodiments also relate to other types of clipping devices including, but not limited to, clips for fastening tissue layers together and clips for closing openings in one or more layers of tissue.

FIGS. 1-9 show a clipping device 100, according to an exemplary embodiment of the invention. As shown in FIG. 1, the clipping device 100 comprises a core member 102 engaging a two-piece hemostasic clip 104 including two or more arms 106. It will be understood by those of skill in the art that the clip 104 may take any shape and size, and may be formed of a variety of materials. The core member 102 may be substantially housed within a capsule 108. The arms 106 are connected to one another via the core member 102, which includes constraint tabs 118 for securing proximal ends 120 of the arms 106. The arms 106 of the clip 104 are biased toward an open, tissue-receiving configuration however, they may be constrained in a tissue gripping configuration by the capsule 108. The capsule 108 is coupled to a bushing 110, which is coupled to a handle (not shown) which remains outside a body of a patient via, for example, a flexible member 114 which slidably receives therethrough a control wire 116 connecting the core member 102 to an actuator (not shown) on the handle. The flexible member 114 may be formed as a coil of wire or any other suitable, flexible structure. The flexible member 14 may be coated, lubricated and/or covered such that the control wire 116 may be easily slid therethrough as would be understood by those skilled in the art.

Figure 2:
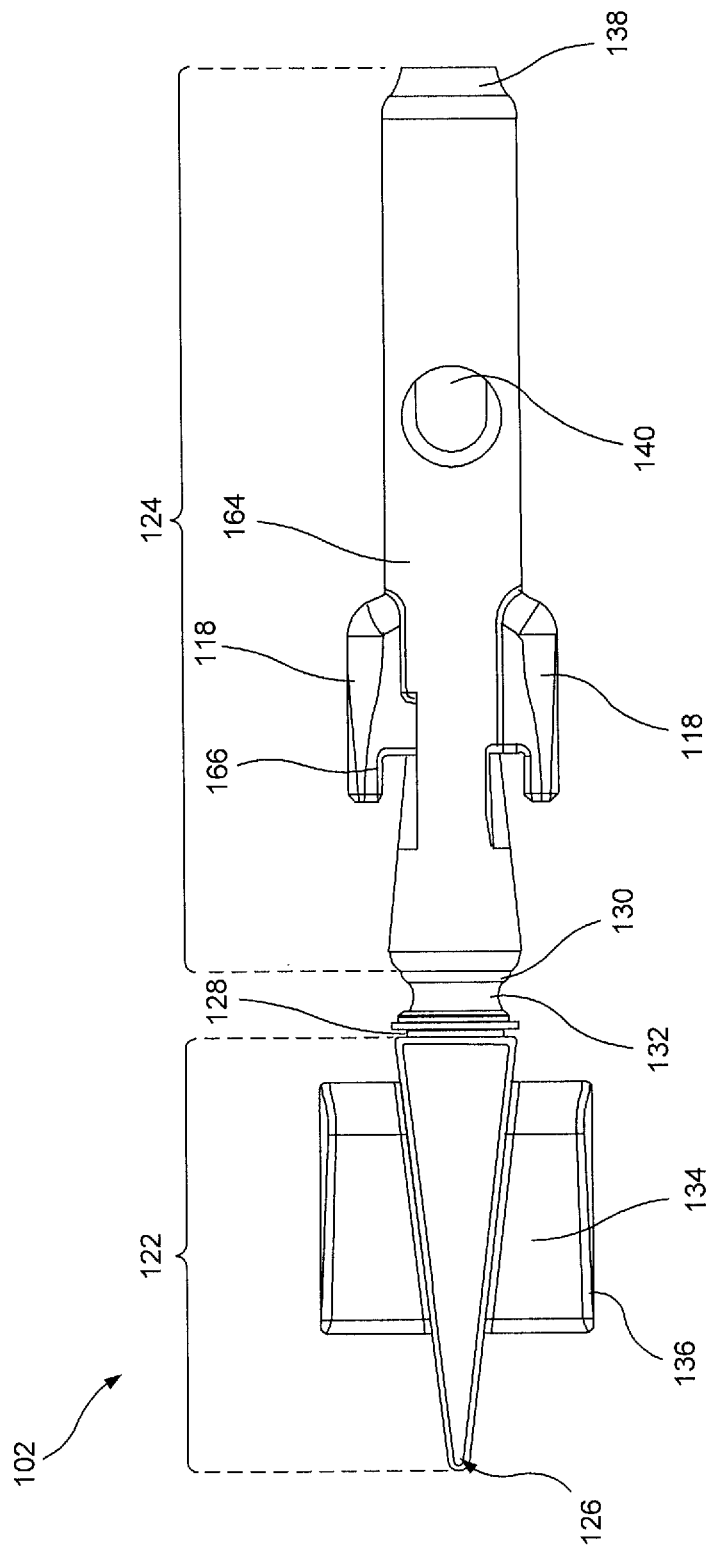
FIG. 2 shows a side view of a core member of the device of FIG. 1.

As shown in FIG. 2, the core member 102 includes a distal portion 122 coupled to a proximal portion 124. The distal portion 122 extends proximally from a tapered distal tip 126 to a proximal end 128 connected to a distal end 130 of the proximal portion 124 via a frangible link 132 designed to fail when subjected to a predetermined load. It will be understood by those of skill in the art that the frangible link may be formed as a weld or other suitable connection so long as the connection remains in place until subjected to the predetermined load and fails when this load is applied. It will also be understood by those of skill in the art that the distal portion 122 and the proximal portion 124 may be two distinct elements such that the frangible link 132 is a connection point therebetween. The distal and proximal portions 122, 124 may be welded, glued or bonded via any other material that is designed to break when subjected to a force of at least a predetermined magnitude. Alternatively, the distal and proximal portions 122, 124 may be connected to one another by mechanical connectors designed to break when subjected to a force of at least the predetermined magnitude. The distal portion 122 may also include protrusions 134 extending along a portion of a length of the distal portion 122 with outer edges 136 of the protrusions 134 substantially parallel to a longitudinal axis of the core member 102. The protrusions 134 may, for example, be located on diametrically opposite sides of the distal portion 122 so that each protrusion 134 engages one of the arms 106 of the clip 104. It will also be understood by those of skill in the art that the protrusions 134 may be sized and shaped to fit within the capsule 108.

The proximal portion 124 extends from the distal end 130 to a proximal end 138. The proximal portion 124 includes the constraint tabs 118, which are positioned on opposite sides of the proximal portion 124. Each constraint tab 118 may protrude from a surface 164 of the proximal portion 124 such that an inner surface 166 of the constraint tab 118 secures the proximal ends 120 of the arms 106 against the surface 164. The proximal portion 124 may further include a hole 140 (shown in FIG. 9) located on a side thereof, proximally of the constraint tabs 118 and a lumen 142 through the core member 106 from the hole 140 to the proximal end 138.

Figure 3:
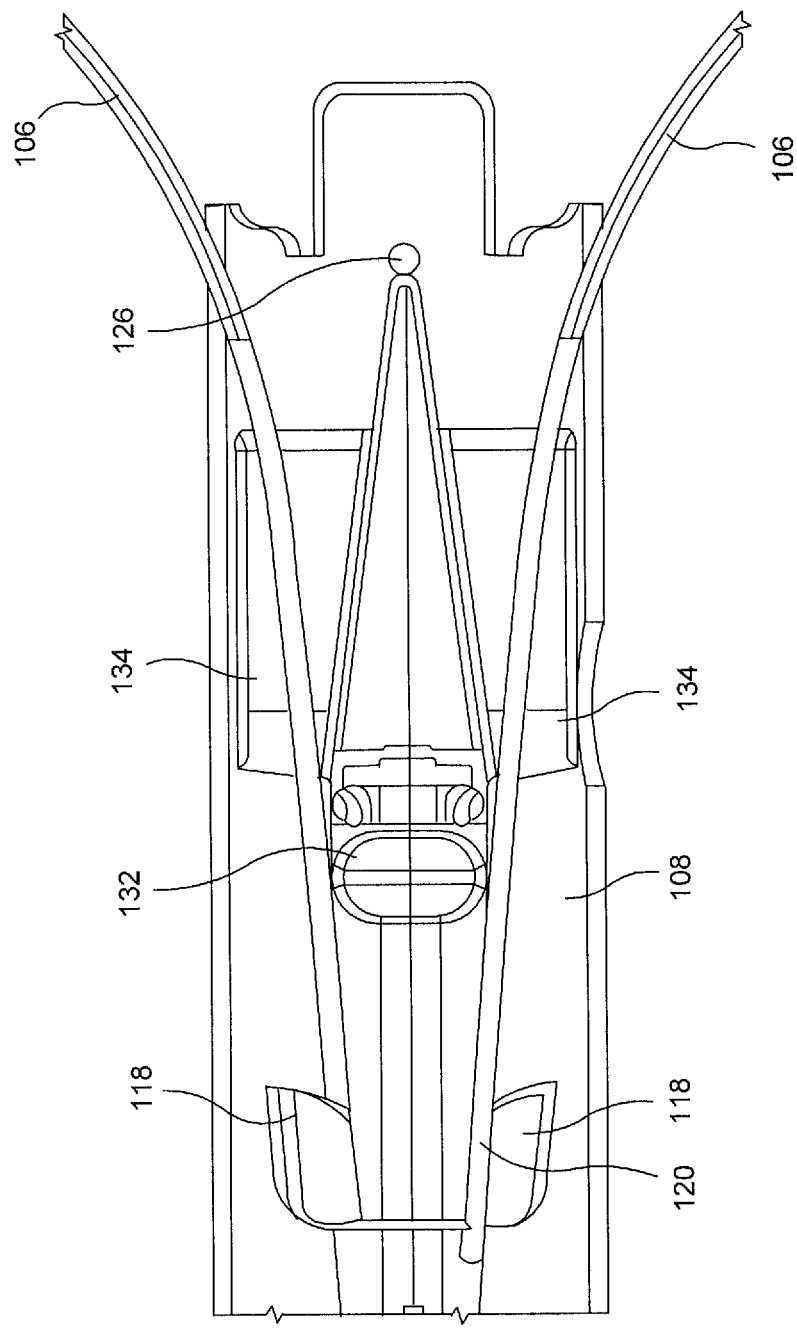
FIG. 3 shows a side view of a distal end of the core member and a proximal end of a clip of the device of FIG. 1.
Figure 4:
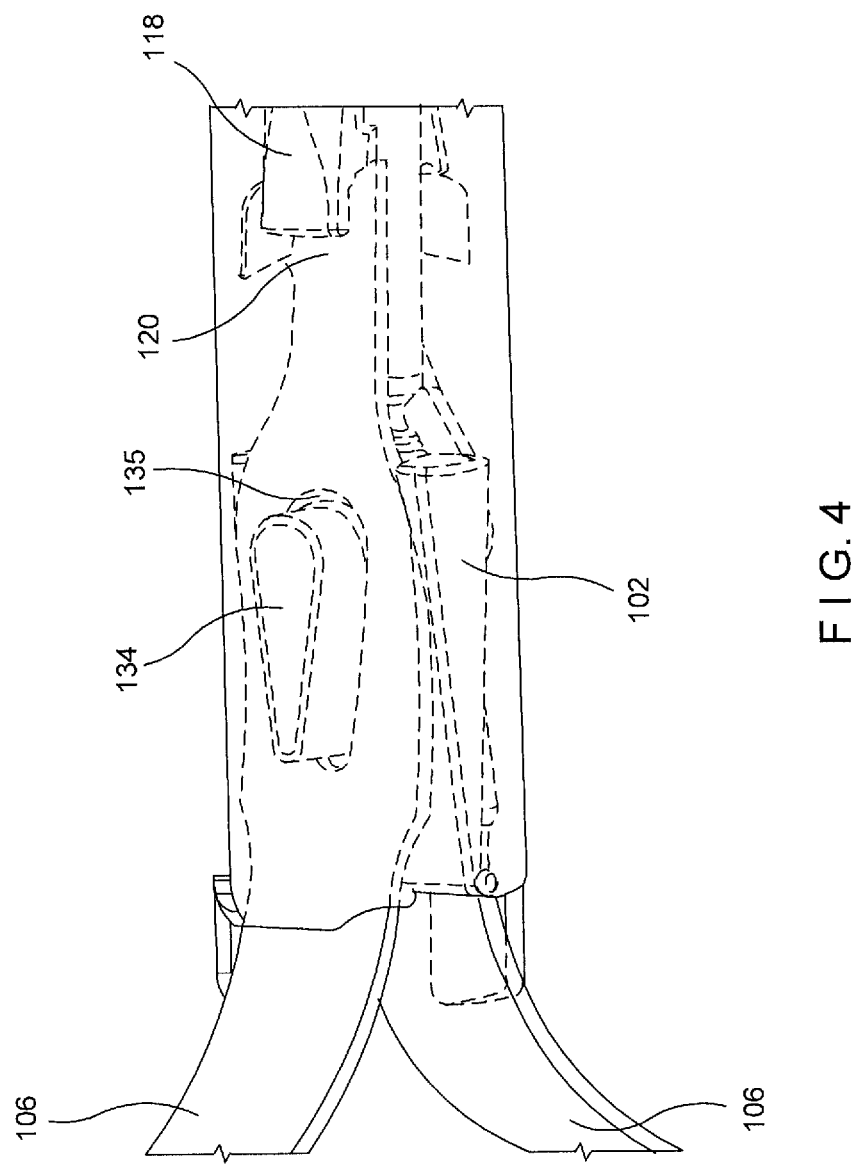
FIG. 4 shows a perspective view of a core member and constraint tab of the device of FIG. 1.

As shown in FIGS. 3 and 4, the protrusions 134 and the constraint tabs 118 may substantially align along a length of the core member 102 such that the proximal ends 120 of the arm 106 are secured by the constraint tabs 118 while a portion of the arms 106 located distally of the proximal ends 120 are engaged by the protrusions 134. Thus, the arms 106 may be substantially aligned along a length of the core member 102. The proximal ends 120 of the arms are formed such that they are engagable by the constraint tabs 118. Distally of the proximal ends 120, in a position along the arms 106 corresponding to the positioning of the protrusions 134, are cut-outs 135 that correspond in shape to the shape of the protrusions 134. For example, the protrusions 134 may be tear-shaped with the cut-outs 135 in the arm 106 shaped to receive the protrusions therein (e.g., also tear-shaped). However, it will be understood by those of skill in the art, that the protrusion 134 and cut-out 135 may be a variety of shapes so long as the protrusions 134 can be received within the cut-outs 135 to engage the arms 106 as desired. Since the arms 106 are aligned along the length of the core member 102, the arms 106 of the clip 104 are able to open and close as the core member 106 is advanced and retracted through the capsule 108.

Figure 5:
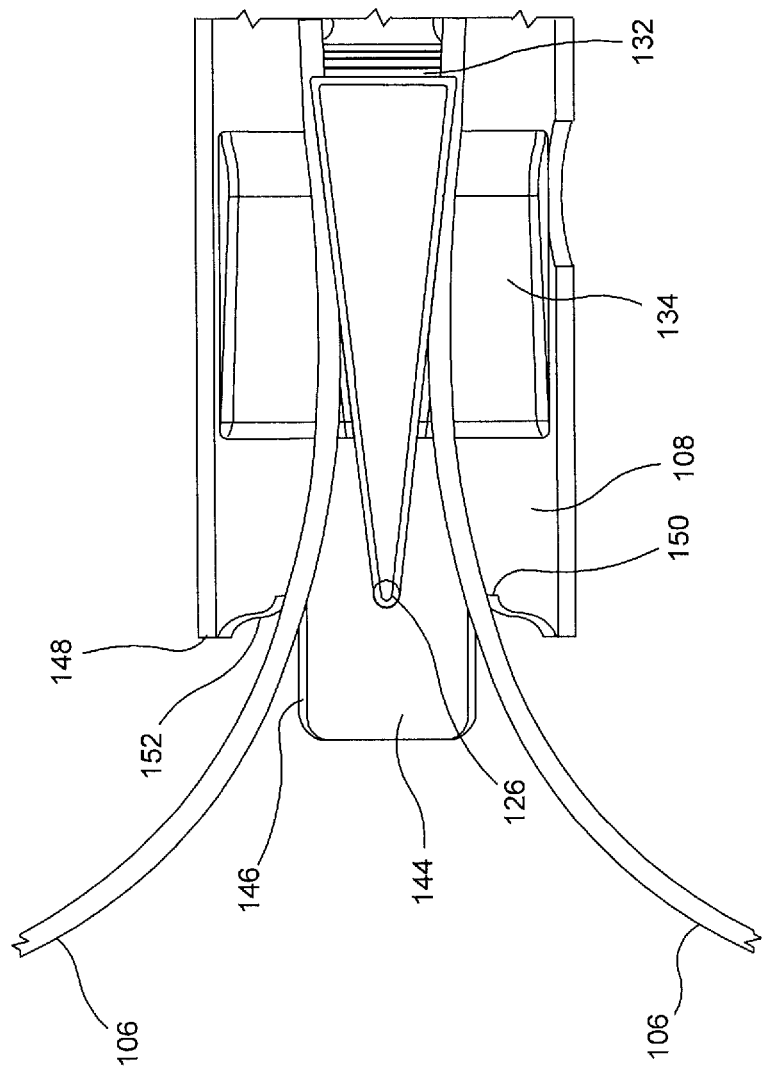
FIG. 5 shows a side view of the distal end of the core member of the device of FIG. 1.

The core member 102 may be substantially housed within the capsule 108 for slidable movement therewithin. In a first configuration, the distal tip 126 of the core member 102 aligns with a base 150 of a capsule tab 144 formed at a distal end 152 of the capsule 108, as shown in FIG. 5. During the manufacturing process, the capsule tab 144 may be bent 90 degrees toward a midline of the capsule 108 such that the core member 102 may not slide distally past the distal end 152 of the capsule 108. It should be noted that FIG. 5 shows the capsule tab 144 in an un-bent configuration for illustrative purposes. The bent capsule tab 144 defines a range of motion for the clip 104, which is shown via arrows in FIG. 5, and controls a plane about which the clip 104 bends around the capsule 108 as the clip 104 is pressed against the tissue, preventing the arms 106 from pushing into the tissue. The bent capsule tab 144 separates the arms 106 such that the arms 106 contact an edge 146 of the capsule tab 144 in the bent configuration. As the device 100 is inserted into a body, the arms 106 are pressed against tissue with the force exerted by the tissue against the arms 106, spreading them apart. However, an edge 148 of the distal end 152 of the capsule 108 limits how far the arms 106 may be bent away from a longitudinal axis of the device 100. The clip plane is selected to maximize a flexibility of the clip while minimizing a risk of plastic deformation of the arms 106.

Figure 6:
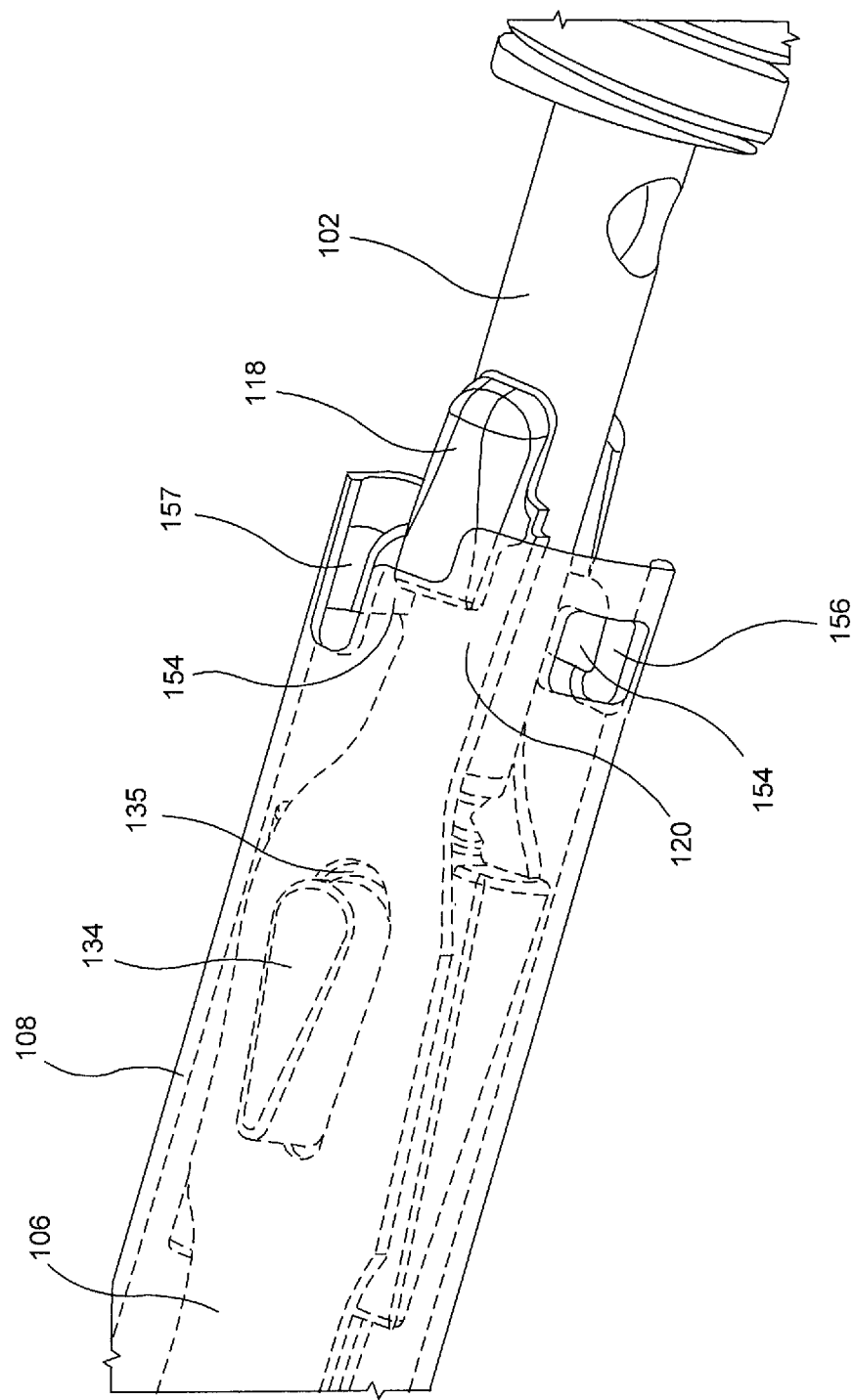
FIG. 6 shows a perspective view of the core member engaging proximal ends of the two-piece clip of the device of FIG. 1.

As shown in FIG. 6, to allow the clip 104 to repeatedly open and close, the proximal ends 120 of the arms 106 are constrained from locking into the capsule 108 until after the clip 104 has been fully deployed. When the proximal ends 120 are secured by the constraining tabs 118, the arms 106 may be repeatedly opened and/or closed so long as the frangible link 132 has not been broken and the clip 104 is not deployed. The proximal ends 120 may include tabs 154, which are engagable by the constraint tabs 118 such that the proximal ends 120 of the arms 106 are secured by the constraint tabs 118. It will be understood by those of skill in the art that the proximal ends 120 may be shaped in any way so long as they are engaged by the constraint tabs 118. However, once the frangible link 132 has been broken (when the pre-determined load is exceeded), the proximal ends 120 are released from the constraint tabs 118 as the distal portion 122 and the proximal portion 124 of the core member 106 separate from one another. The released proximal ends 120 then lock into the capsule windows 156. For example, the tabs 154 project through the capsule windows 156, keeping the clip 104 in position relative to the capsule 108.

Figure 7:
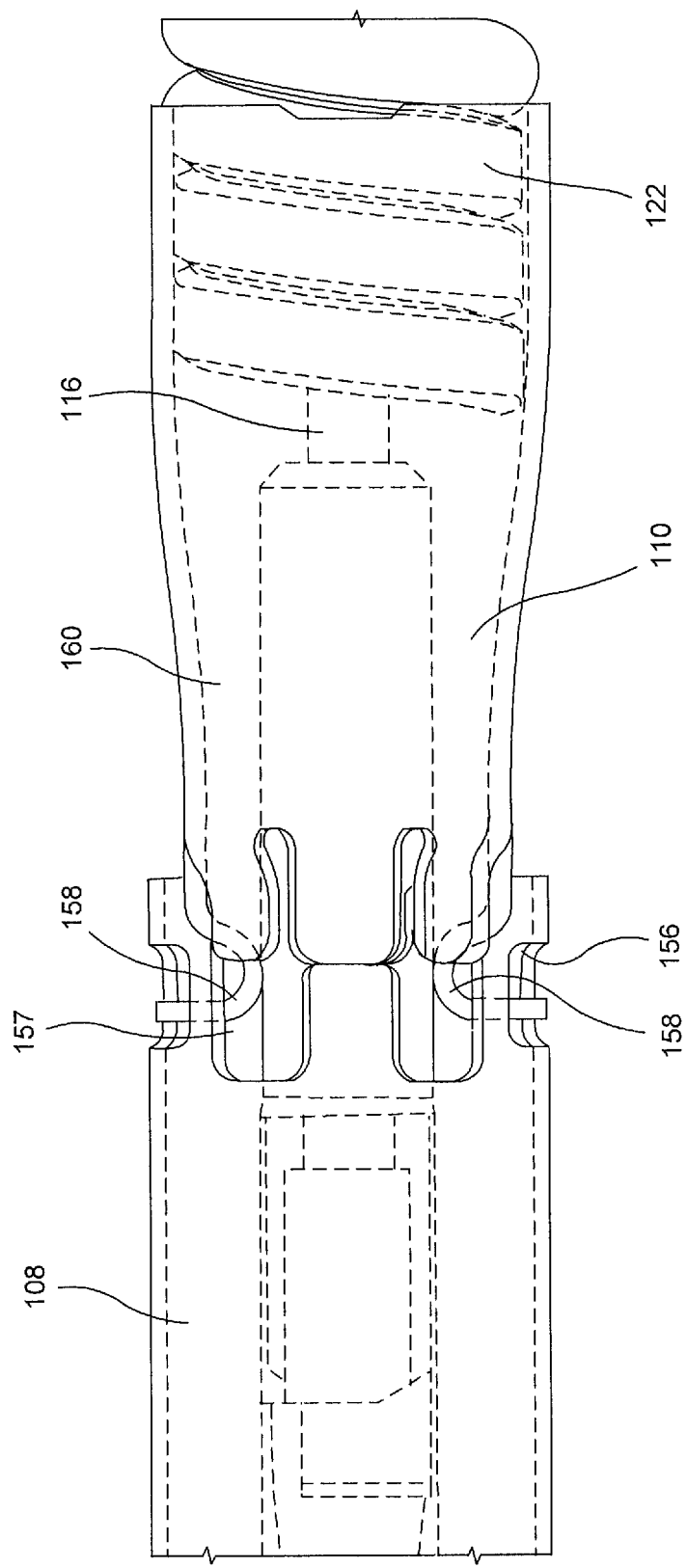
FIG. 7 shows a side view of a capsule and a bushing of the device of FIG. 1 in an engaged configuration.
Figure 8:
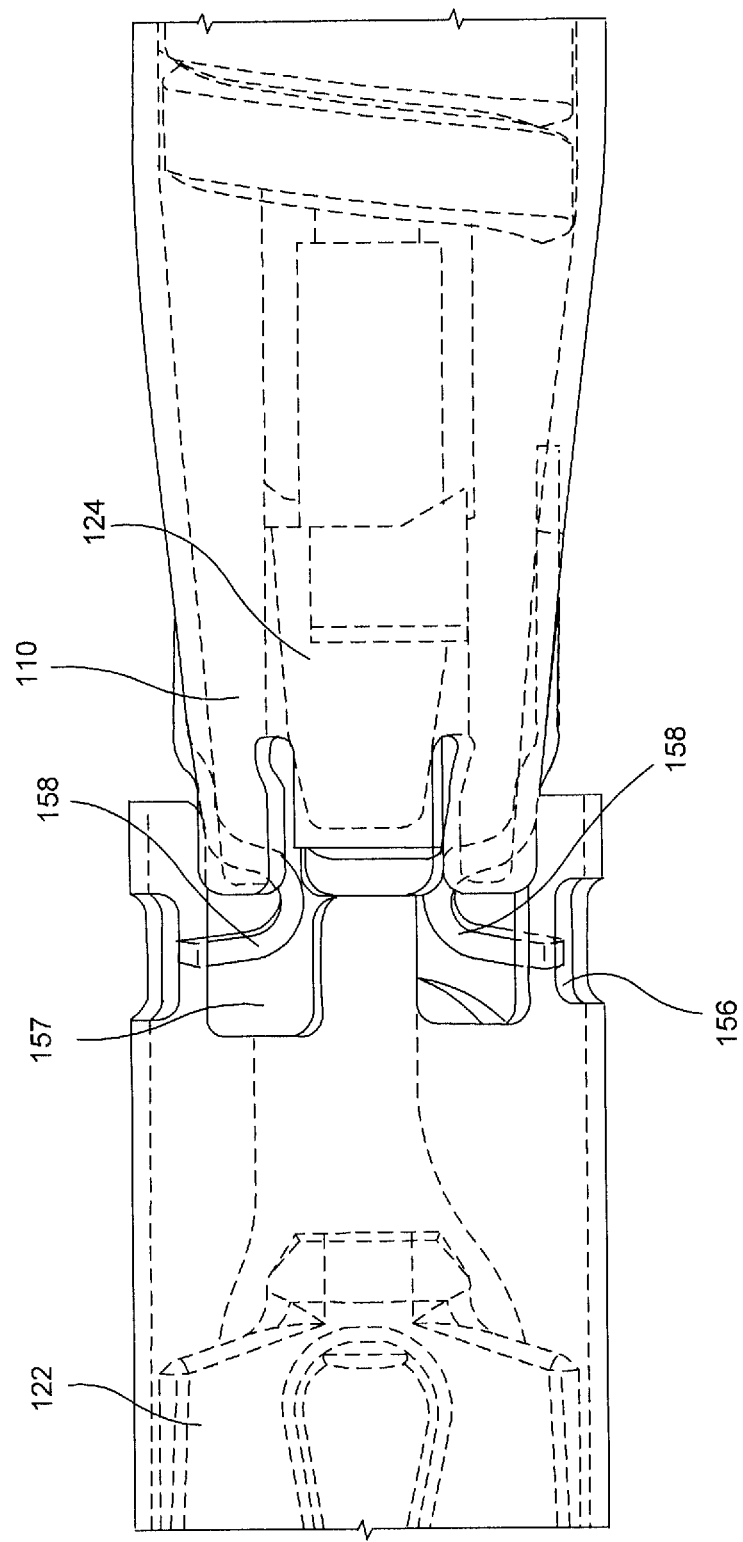
FIG. 8 shows a side view of the capsule and the bushing of the device of FIG. 1 disengaging from one another.

As shown in FIGS. 7 and 8, the capsule 108 is coupled to the bushing 110, which may include cantilever arms 158. The cantilever arms 158 are biased towards a centerline of the bushing 110, but are moved radially outward when the proximal portion 124 is received within the bushing 110. When the proximal portion 124 is slid through the bushing 110, the proximal portion 124 forms a plug which pushes the cantilever arms 158 radially outward maintaining them in a locked position binding the bushing 110 to the capsule 108 as the arms 158 engage the capsule windows 156, as shown in FIG. 7. After the core member 102 has been severed (i.e., after the frangible link 132 has been broken) and the proximal portion 124 is drawn proximally through the capsule 108 and the bushing 110, the cantilever arms 158 are no longer supported by the surface 164 of the proximal portion 124 and thus return to their biased position towards the centerline of the bushing 110. At this point, the arms 158 release the windows 156 of the capsule 108, separating the bushing 110 from the capsule 108. At this point, the proximal ends 120 of the arms 106 engage the capsule 108 via clip windows 157 in the capsule 108 locking the clip arms 106 in the closed position.

Figure 9:
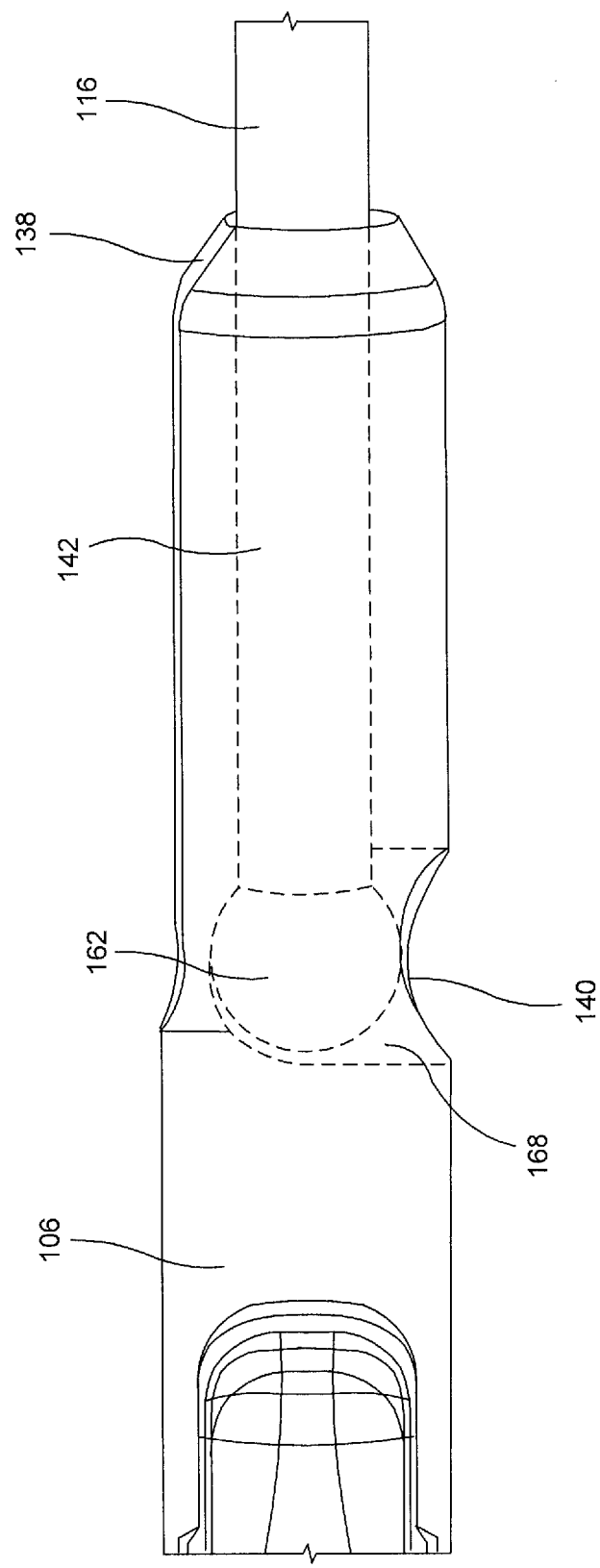
FIG. 9 shows a side view of a distal end of a control wire connected to the core member of the device of FIG. 1.

The core member 102 may be drawn proximally by the control wire 116, which may be coupled to the core member 102, which is in turn connected to the clip 104. Thus, drawing the control wire 116 proximally and distally through the capsule 108 and the bushing 110 controls the repeated opening and closing of the arms 106 of the clip 104. As shown in FIG. 9, the control wire 116 may include a ball 162 at a distal end thereof. A diameter of the ball 162 may be greater than a diameter of the control wire 116. A length of the control wire 116 may be inserted through the hole 140 located on the side of the core member 106 and slid through the lumen 142, which is sized and shaped to accommodate the length of the control wire 116 and extends proximally of the hole 140, until the ball 162 is also inserted into the hole 140. A diameter of the lumen 142 is smaller than the diameter of the ball 162 such that the ball 162 abuts a distal end 168 of the lumen 142 and is captured in the core member 102 with a longitudinal axis of the core member 102 substantially aligning with a longitudinal axis of the control wire 116. Thus, drawing the control wire 116 proximally draws the core member 102, and thereby the clip 104, proximally relative to the capsule 108 and the bushing 110.

As the control wire 116 is drawn proximally, the arms 106 are drawn into the capsule 108 so that contact with the edge of the capsule 148 draws distal ends 112 of the arms 106 toward one another, compressing any tissue received therebetween. As seen in FIG. 1, distal ends 112 of the arms 104 are wider than proximal ends 120, thereby defining a maximum extent to which the arms 106 may be drawn into the capsule 108. Thus, as the control wire 116 is drawn proximally and the distal ends 112 of the arms 106 approach one another, the force required to compress any tissue gripped thereby applies a load to the control wire 116. After the arms 106 have been drawn into the capsule 108 to the maximum extent, operating the actuator to draw the control wire 116 further proximally applies an increasing amount of force to the control wire 116, and consequently, to the proximal portion 124 of the core member 102. Once the predetermined load has been reached, the frangible link 132 is broken such that the control wire 116 and proximal portion 124 continue to move proximally relative to the arms 104 and the distal portion 122, which remain within the capsule 108. As described above, once the frangible link 132 has been broken, the cantilever arms 158 are no longer supported by the outer diameter of the proximal portion 124 and return to their biased position toward the centerline of the bushing 110, separating the bushing 110 from the capsule 108.

The following embodiments of the present invention are substantially similar to the device 100 except for the differences specifically called out and, as will be understood by those of skill in the art, the following devices may be used In substantially the same manner as described above. Specifically, core members housed substantially within a capsule releasably coupled to a bushing until deployment are coupled to a control wire (or other tensioning member), which may be drawn proximally to draw the arms of the clip into the capsule until the pre-determined load breaks a frangible link, locking the clip in the closed position and separating the capsule from the bushing. The following embodiments include core members with structural differences and which are, for example, coupled to the tensioning member in various ways.

Figure 10:
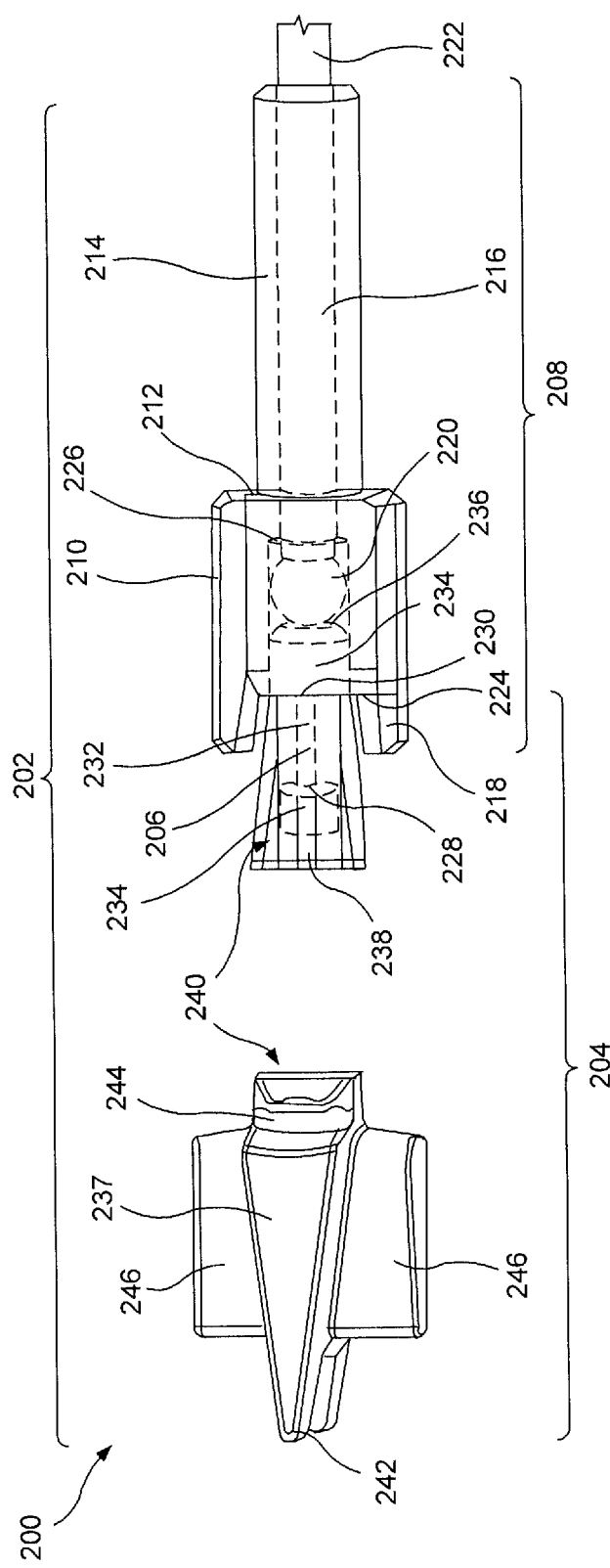
FIG. 10 shows a side view of a core member of a device according to a second embodiment of the invention in a fractured configuration.
Figure 11:
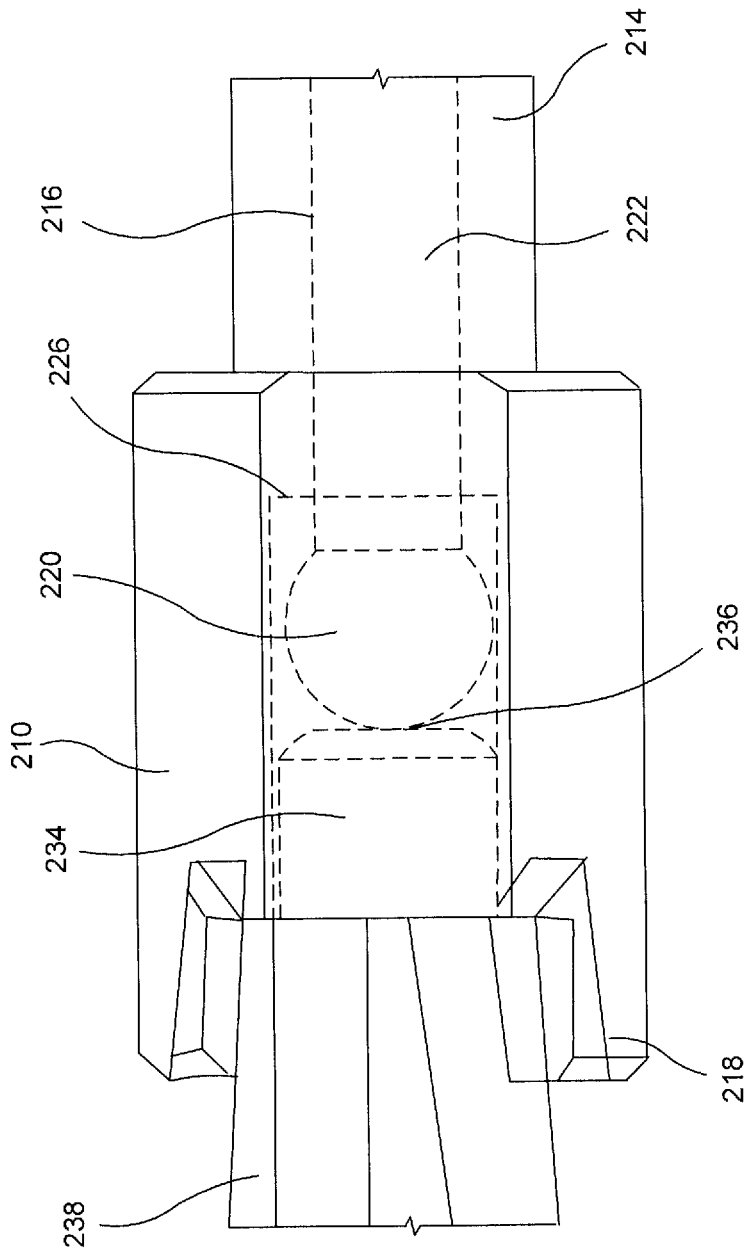
FIG. 11 shows a side view of the control wire of the device of FIG. 10 connected to the core member.

As shown in FIG. 10, a device 200, according to another embodiment of the invention, comprises a core member 202 engaging a two-piece hemostasis clip (not shown). The core member 202 comprises a first member 204, a second member 206 and a third member 208. The first member 204 may be formed, for example, of a molded material while the second member 206 and the third member 208 may, for example, be screw machined. It will be understood by those of skill in the art, however, that any fabrication means may be used to form the first, second and third members 204, 206, 208. The third member 208 may include a constraining portion 210 connected to a distal end 212 of a longitudinal portion 214. A lumen 216 may extend through both the constraining portion 210 and the longitudinal portion 214. The constraining member 210 may include constraining tabs 218 at a distal end 224 thereof, positioned, for example, on opposite sides of the constraining member 210 to secure the proximal ends of the two arms of the two-piece clip. As shown in FIG. 11, the constraining member 210 is adapted to hold a ball tip 220 at a distal end of a control wire 222 inserted through the lumen 216 via the distal end 224 of the constraining portion 210. The ball tip 220 may be held by the constraining portion 210 by a shoulder 226 within the lumen 216. The shoulder 226 is formed such that a diameter of the lumen 216 proximal of the shoulder is smaller than a diameter of the lumen 216 distal of the shoulder 226 and a diameter of the ball tip 220. Therefore, a proximal end (not shown) of the control wire 222 is inserted through the distal end 224 of the constraining member 210 and slid along the third member 208 within the lumen 216 until the ball tip 220 abuts the shoulder 226.

Once the control wire 216 and the ball tip 220 have been appropriately positioned within the third member 208, the second member 206 may be overmolded with the first member 204 and then welded to an inner diameter of the lumen 216 at the distal end 224 of the third member 208. The second member 206 may be formed such that the overmolded plastic of the first member 204 retains a load greater than that required to fracture a frangible link 240. For example, the second portion 206 may be shaped as a barbell with a rod 232 coupling first and second expanded portions 234 at a distal and proximal ends 228, 230, respectively, thereof. The second expanded portion 234 (at the proximal end 230) may be welded within the lumen 216 so that a proximal surface 236 of the second portion 206 abuts the ball tip 220, securing the ball tip 220 and the control wire 222 in place. Although the first, second and third members 204, 206, 208 are described as connected to one another via overmolding and/or welding, it will be understood by those of skill in the art that the first, second and third members 204, 206, 208 may be connected to one another by any other suitable connection means.

The first member 204 includes a distal portion 237 coupled to a proximal portion 238 via a frangible link 240. The distal portion 237 may be shaped such that it extends from a tapered tip 242 at a distal end thereof to a proximal end 244. Protrusions 246 extend from opposite sides of the distal portion 237 along a portion of the length thereof. The protrusions 246 may be substantially aligned with the constraining tabs 218 of the first member 204 such that they engage corresponding cutouts in the arms (not shown) of the clip, limiting the opening stroke of the arms and, together with the constraining tabs 218, maintaining the alignment and orientation of the clip in a manner similar to that described above.

Figure 12:
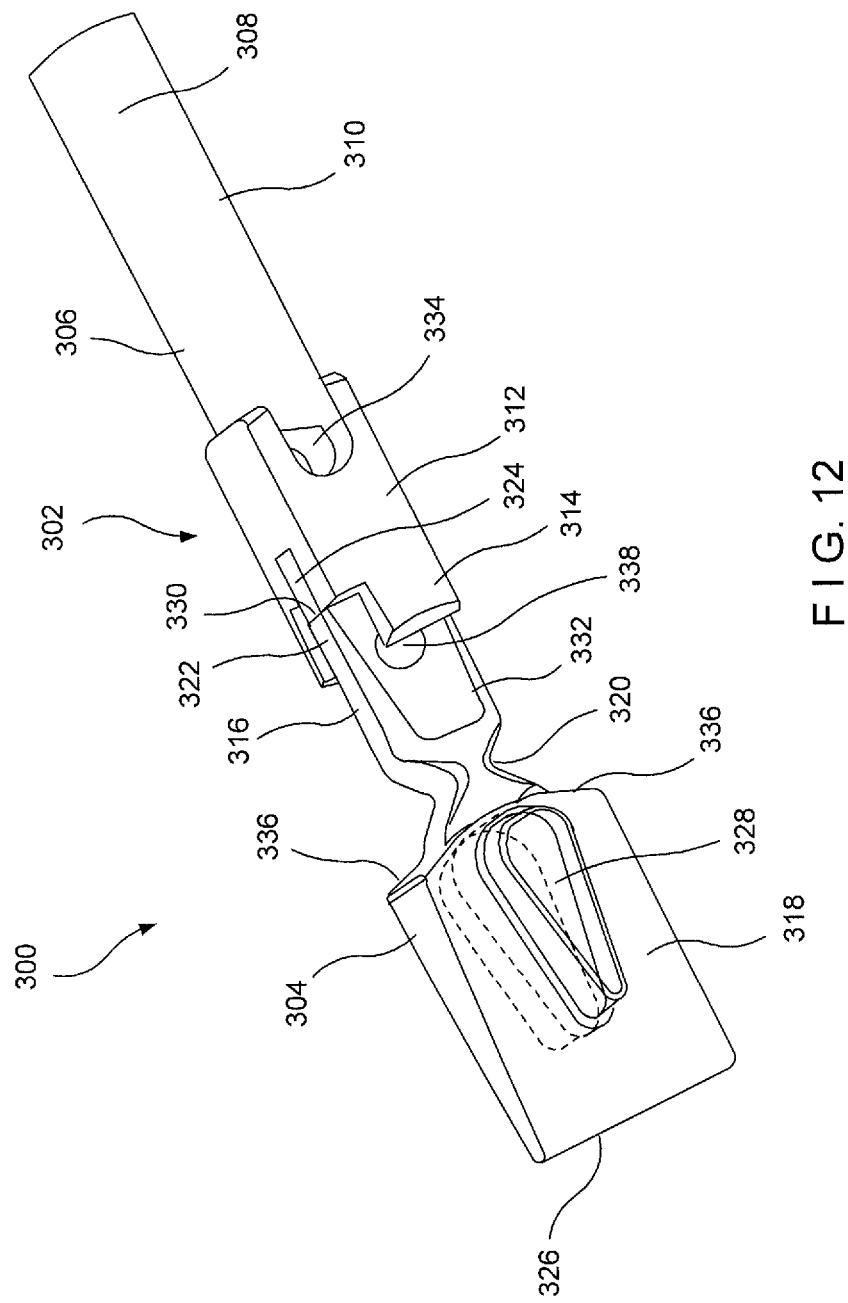
FIG. 12 shows a perspective view of a device according to a third embodiment of the invention.

As shown in FIG. 12, a device 300, according to another embodiment of the invention, comprises a core member 302 engaging arms of a two-piece clip (not shown). The core member 302 further comprises a first member 304 and a second member 306. The first member 304 may be molded while the second member 306 may be machined such that the first member 304 may be slid into a constraining portion 312 of the second member 306 and locked with a crosspin (not shown). It will be understood by those of skill in the art, however, that the core member 302 may be formed via any other suitable manufacturing method. The second member 306 further includes a longitudinal portion 310 with the constraining portion 312 at a distal end thereof and a lumen 308 extending therethrough. The lumen 308 is sized and shaped to accommodate a control wire or other tensioning member (not shown) and may include a lateral hole 334 at a distal end thereof for receiving the control wire. Thus, the constraining portion 312 may house a ball-tipped end of the control wire such that the control wire may be slid through the lumen 308 of the longitudinal portion 310 via the hole 334 until the ball-tipped end of the control wire abuts the distal end of the lumen 308.

The constraining portion 312 includes constraining tabs 314 at a distal end thereof for securing proximal ends of arms of the clip. The constraining tabs 314 are formed on opposite sides of the constraining portion 312 to secure proximal ends of the arms by pressing the arms against a proximal portion 316 of the first member 304. The proximal portion 316 of the first member 302 may include an engaging member 322 substantially planar to engage a substantially longitudinal notch 324 in the constraining member 312. The crosspin may be inserted through a lateral opening (not shown) of the constraining portion 312 and a corresponding hole 338 of the engaging member 322 to fix the first member 304 relative to the second member 306.

The first portion 302 further includes a distal portion 318 connected to the proximal portion 316 via a frangible link 320 designed to fracture when subjected to a load of at least a predetermined magnitude. A strong attachment between the first and second members 304, 306, respectively, ensures that the first and second members 304, 306, respectively, will not detach from one another until the frangible link 320 is broken through the application of the predetermined load. The distal portion 318 which extends from a tapered tip 326 at a distal end thereof to a proximal end 336 further includes protrusions 328 formed on opposite sides thereof substantially aligned along a length of the core member 302 with the constraining tabs 314. Thus, the proximal ends of the clip arms are secured by the constraining tabs 314 and each of the protrusions 328 engages a corresponding cut-out on the arm such that the protrusions 328 and the constraining tabs 314 aid in the alignment and orientation of the arms.

Figure 13:
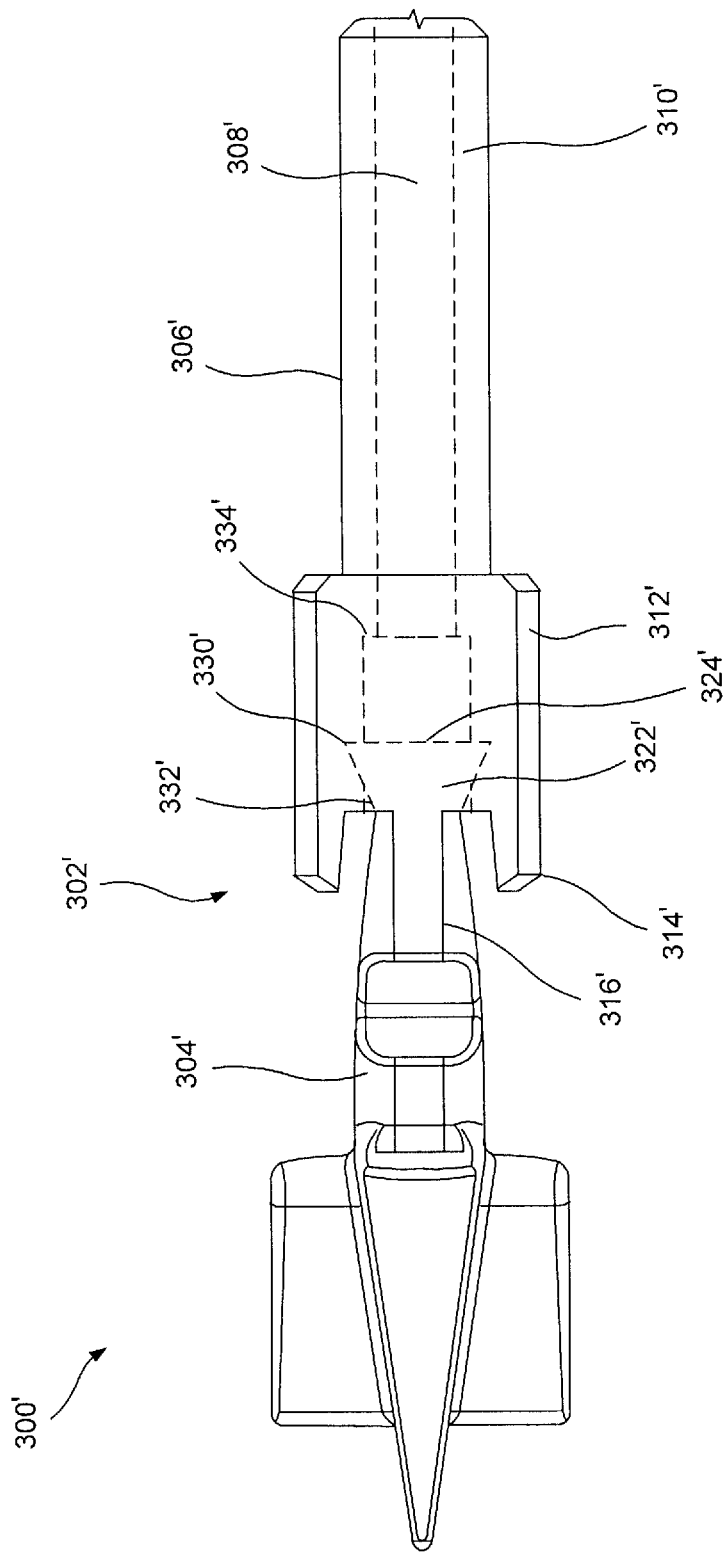
FIG. 13 shows a side view of an alternate embodiment of the device of FIG. 12.

A device 300', as shown in FIG. 13, may be substantially similar to the device 300 as described above, comprising a core member 302' including a first member 304' and a second member 306'. The first member 304' may be substantially similar to the first member 304 and the second member 306' may be substantially similar to the second member 306. The core member 302' differs, however, in a connection between the first member 304' and the second member 306'. An engaging portion 322' and a notch 324' of a constraining member 312' may be correspondingly shaped such that a crosspin is not necessary to fix the first member 304' relative to the second member 306' of the core member 302'. The engaging portion 322' may be sized and shaped to maximize the attachment strength of the first member 304' to the second member 306', while maintaining a space between a proximal portion 316' and constraining tabs 314' for securing proximal ends of the arms. For example, the engaging portion 322' may be shaped such that it interlaces with the notch 324' of the constraining portion 312'. The engaging portion 322' may be shaped such that the proximal end 330' is greater in diameter than a distal end 332' of the engaging portion 322' so that a fracture will not occur between the first member 304' and the second member 306'.

The second member 306' further includes a longitudinal portion and a lumen 308' extending therethrough with an opening at a distal end thereof. The lumen 308' is sized and shaped to accommodate a control wire (not shown) and may include a shoulder 334' within the constraining portion 312' formed such that a diameter of the lumen 308' proximal of the shoulder 334' is smaller than a diameter of the lumen 308' distal of the shoulder 334'. Thus, the constraining portion 312' may house a ball-tipped end of the control wire such that the control wire may be slid through the lumen 308' via the distal opening until the ball-tipped end of the control wire abuts the shoulder 334' as described above. It will be understood by those of skill in the art that the control wire will be fixed in place within the constraining portion 312' by the shoulder 334' and the proximal end 330' of the engaging portion 322'.

Figure 14:
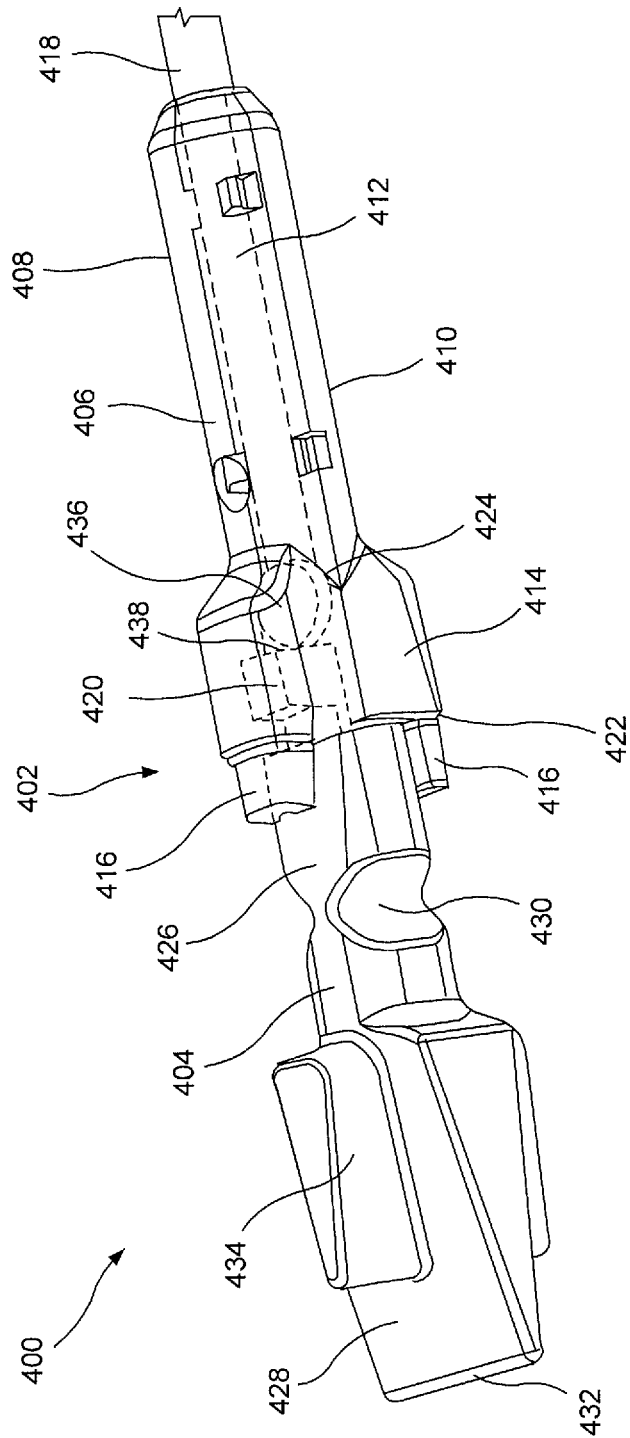
FIG. 14 shows a side view of a device according to a fourth embodiment of the invention.

As shown in FIG. 14, a device 400, according to another embodiment of the present invention, comprises a core member 402 for engaging arms of a clip (not shown), including a first member 404 and a second member 406. The second member 406 may be further comprised of first and second halves 408, 410, respectively, which may be substantially identical to one another and which may be connected to one another to hold a control wire 418 as well as an engaging portion 420 of the first member 404 therewithin. Each of the first and second halves 408, 410, respectively, may be formed of a plastic or a metal material. The first half 408 and the second half 410 may be connected to one another using any number of known securing techniques such as laser welding, RF welding, adhesives, etc., to form the lumen 412. Once connected, the first and second halves 408, 410, respectively, form the second member 406, which includes a lumen 412 extending therethrough. A portion of the lumen 412 extending through a constraining portion 414 formed at a distal end 422 of the second member 406 includes a shoulder 424 extending therein and reducing a diameter of a portion of the lumen 412 proximal of the shoulder 424 relative to the diameter of the lumen 412 distally thereof. This enables the constraining portion 414 to house a ball-tipped end 436 of the control wire 418, which is larger in diameter than a remaining length of the control wire 418 extending proximally of the shoulder 424. Thus, the ball-tipped end 436 may abut the shoulder 424. Each of the first and second halves 408, 410, respectively, includes a constraining tab 416 at a distal end thereof positioned on opposite sides of the second member 404 so that each constraining tab 416 may secure an arm of a two-piece hemostasis clip.

The second member 406 may also include means for engaging the first member 404. For example, the second member 404 may engage the first member 402 via protrusions on an inner surface of the constraining member 414 engaging corresponding indentations on an outer surface of the first member 402. Similarly, the first member 402 may include protrusions on an outer surface thereof while the second member 404 includes corresponding indentations on an inner surface thereof. It will be understood by those of skill in the art that a variety of securing methods may be used for engaging the first member 404 within the distal end 422 of the second member 406. It will also be understood by those of skill in the art that the first member 404 may be engaged within the second member 406 such that a proximal end 438 of the first member 404 abuts the ball-tipped end 436, keeping the control wire 418 from moving within the core member 402.

The first member 404 may be substantially similar to the first member 302 described in regard to the core member 300. Specifically, the first member 404 includes a proximal portion 426 and a distal portion 428 connected to one another via a frangible link 430 which is severed when subjected to a load of at least a predetermined magnitude. The proximal portion 426 is adapted to engage the second member 404 such that the constraining tabs 416 secure proximal ends of the clip by pressing the arms against the proximal portion 426 of the first member 402. The distal portion 428 may be tapered to include a tapered tip 432 and protrusions 434 on opposite sides of the first member 402 such that each protrusion aligns along a longitudinal axis with each constraining tab 416 so that each protrusion engages a cut-out in the arm of the clip, aiding in alignment and orientation of the clip arms.

Figure 15:
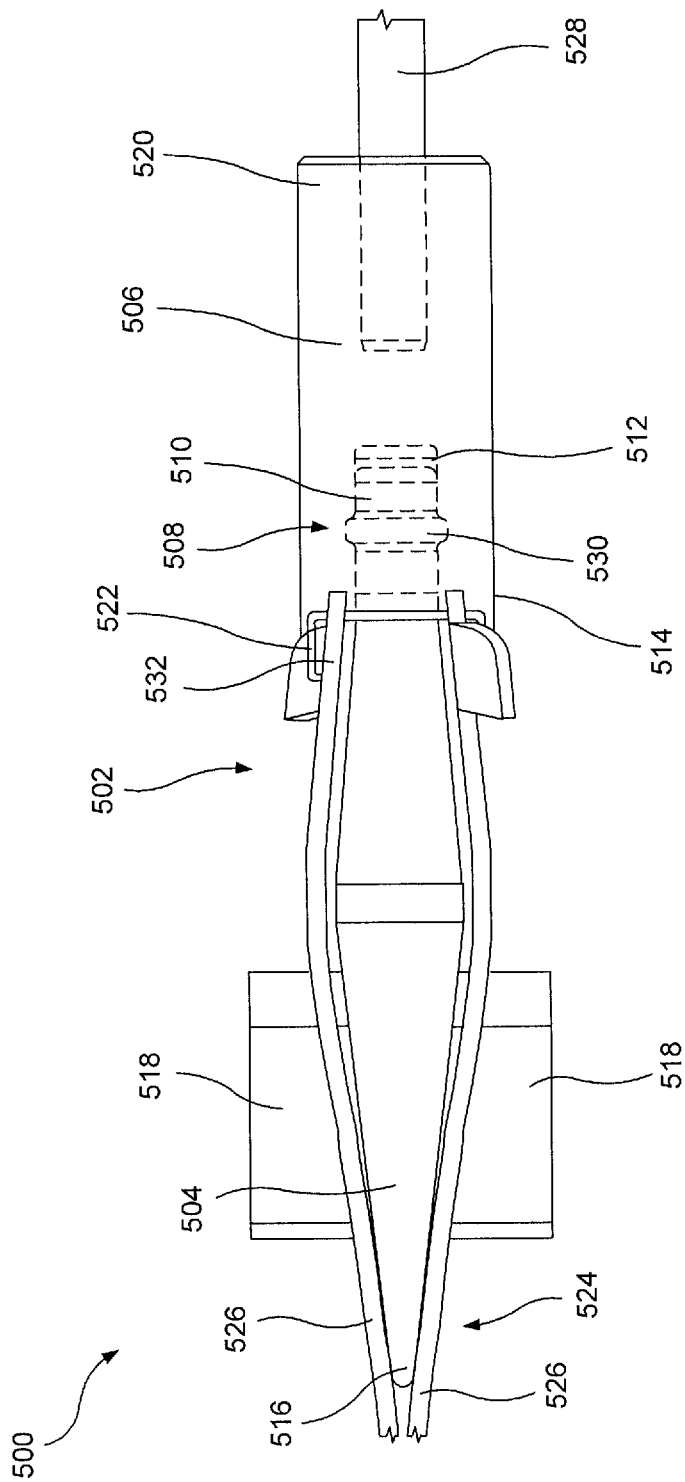
FIG. 15 shows a side view of a device according to a fifth embodiment of the invention.

As shown in FIG. 15, a device 500 according to another embodiment of the present invention, comprises a core member 502 for securing arms 526 of a clip 524, including a first member 504 and a second member 506 coupled to one another via a snap mechanism 508. Similarly to the devices 300, 400, the first member 504 of device 500 includes a tapered tip 516 and protrusions 518 formed proximally of the tapered tip 516 on opposite sides of the first member 502 for engaging arms of the clip. A proximal end 510 of the first member 504 may be adapted to engage a distal end 514 of the second member 506 via the snap mechanism 508. The second member 506 may be substantially longitudinal such that while the distal end 514 may be adapted to engage the proximal end 510 of the first member 504, the proximal end 520 may be adapted to accommodate a control wire 528. The control wire 528 may be connected to the proximal end 520 of the second member 506 by a variety of means including, for example, overmolding, laser welding, etc. It will also be understood by those of skill in the art that the second member 506 may also include a hole and a lumen for accommodating a control wire 528 with a ball tip, as described above in regard to the device 100 and as shown in FIG. 9. The second member 504 also includes constraining tabs 522 at the distal end 514 for securing proximal ends 532 of the arms 526 of the clip 524.

The snap mechanism 508 may include mating features on the proximal end 510 of the first member 504 and the distal end 514 of the second member 506. The mating features may include a radial protrusion 530 around the proximal end 510 and a correspondingly shaped indentation 512 within the distal end 514. It will be understood by those of skill in the art that the core member 502 may include any variety of snap mechanisms 508 so long as the snap mechanism 508 includes mated features that engage one another maintaining the bond between the first and second members 504, 506, respectively, until they are un-snapped when subjected to a load of at least a predetermined magnitude. Thus, the snap mechanism 508 acts as the frangible link of core member 502. It will also be understood by those of skill in the art, however, that the snap mechanism 508 may be formed to maintain the bond between the first and second members 504, 506, respectively, even when subjected to loads greater than the predetermined magnitude. The frangible link in such a device may be formed in the core member 502 in the manner of any of the previously described embodiments, for example, in regard to core members 300 and 400.

Figure 16:
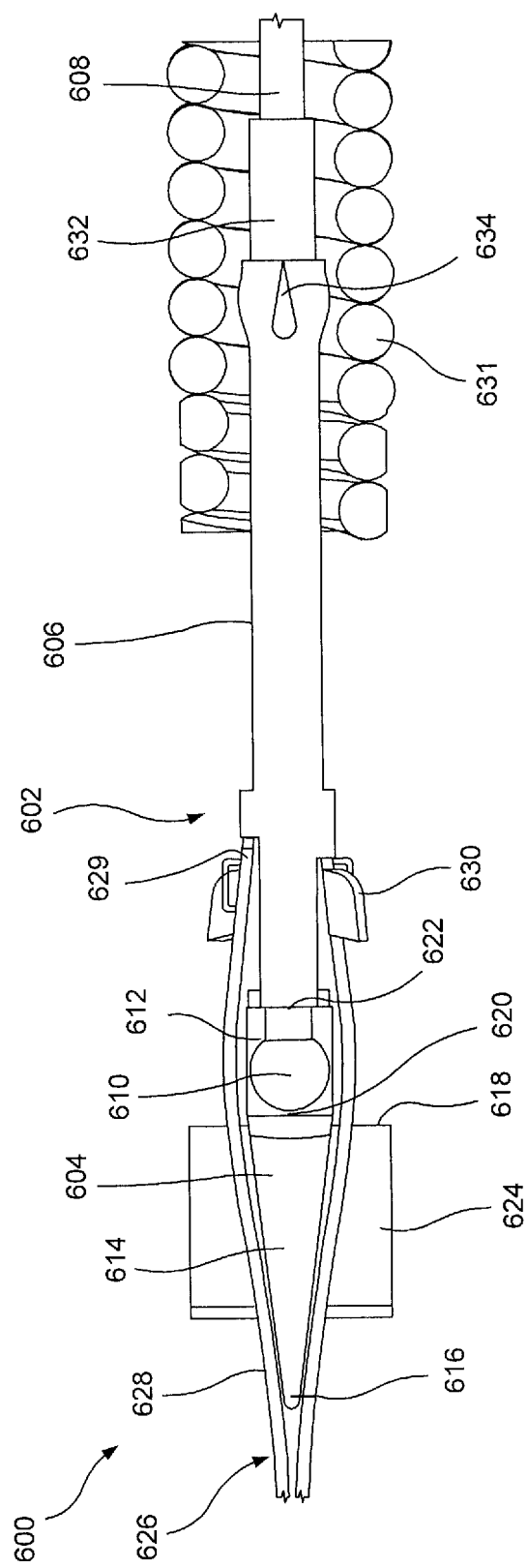
FIG. 16 shows a side view of a device according to a sixth embodiment of the invention.
Figure 17:
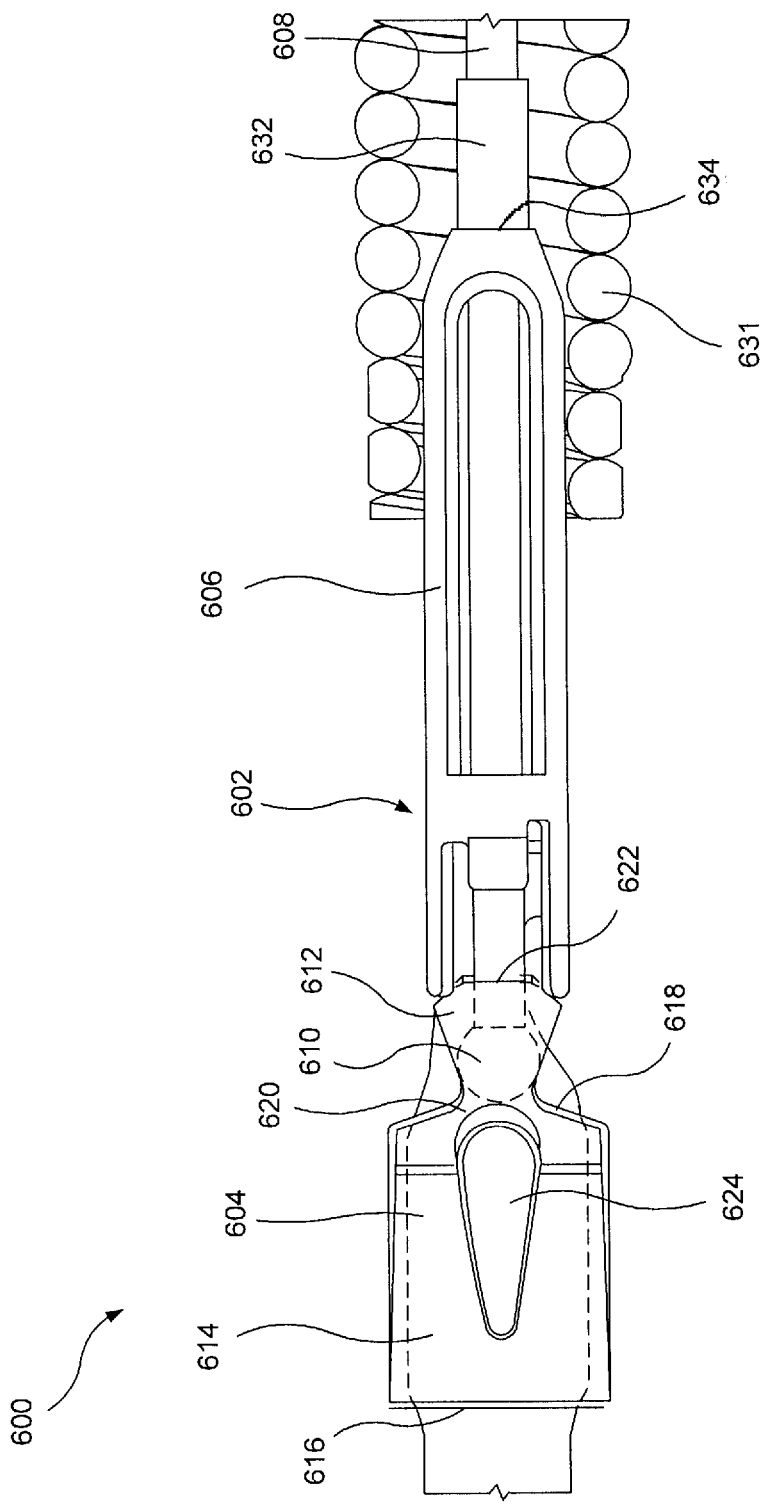
FIG. 17 shows a side view of the device of FIG. 16 rotated relative to FIG. 16 about a longitudinal axis of the device.

As shown in FIGS. 16 and 17, a device 600 according to a further embodiment of the present invention comprises a core member 602 including first and second portions 604, 606, respectively, and a control wire 608. The first portion 604 of the core member 602 may be substantially similar to that of any of the previously described embodiments. Specifically, the first portion 602 may include a proximal portion 612 and a distal portion 614. The distal portion 614 may be tapered such that it extends from a tapered tip 616 to a distal end 618 that is connected to the proximal portion 612 via a frangible link 620 designed to sever when subjected to a load of at least a predetermined magnitude. Further, the distal portion 616 includes protrusions 624 for engaging arms 628 of a clip 626. The first portion 604 differs from previously described embodiments, however, in that a distal end 610 of the control wire 608 may be molded into proximal portion 612 while a remaining length of the control wire passes through the second portion 606, which may be substantially longitudinal such that a distal end 622 of the second portion 606 abuts the proximal portion 612.

The second portion 606 includes constraint tabs 630 for securing proximal ends 629 of the arms 628 that substantially align with the position of the protrusions 624 of the first portion 604 such that the clip 626 may be properly aligned and oriented while limiting an opening stroke via a surface of the arms 628. The second portion 606 may be formed, for example, of a portion of laser cut hypotube reformed after cutting or stamped and rolled and is designed to be collapsible when the control wire 608 pulls the second portion 606 into a flexible member 631 (e.g., coil). The second portion 606 is adapted and configured to collapse as the second portion 606 comes into contact with an inner surface of the flexible member 631. The core member 602 is held in place by a hypotube 632 positioned proximally of a proximal end 634 of the second portion 606 such that when the control wire 608 is drawn proximally, the proximal end 634 remains in position causing the second portion 606 to collapse as the control wire 608 is slid therethrough. For example, the hypotube 632 may be welded, or otherwise secured to the control wire 608. The distal end 610 of the control wire 608 is coupled to the first portion 604 (e.g., molded therein) so the first portion 604 is drawn closer to the flexible member 631 as the second portion 606 collapses.

Figure 18:
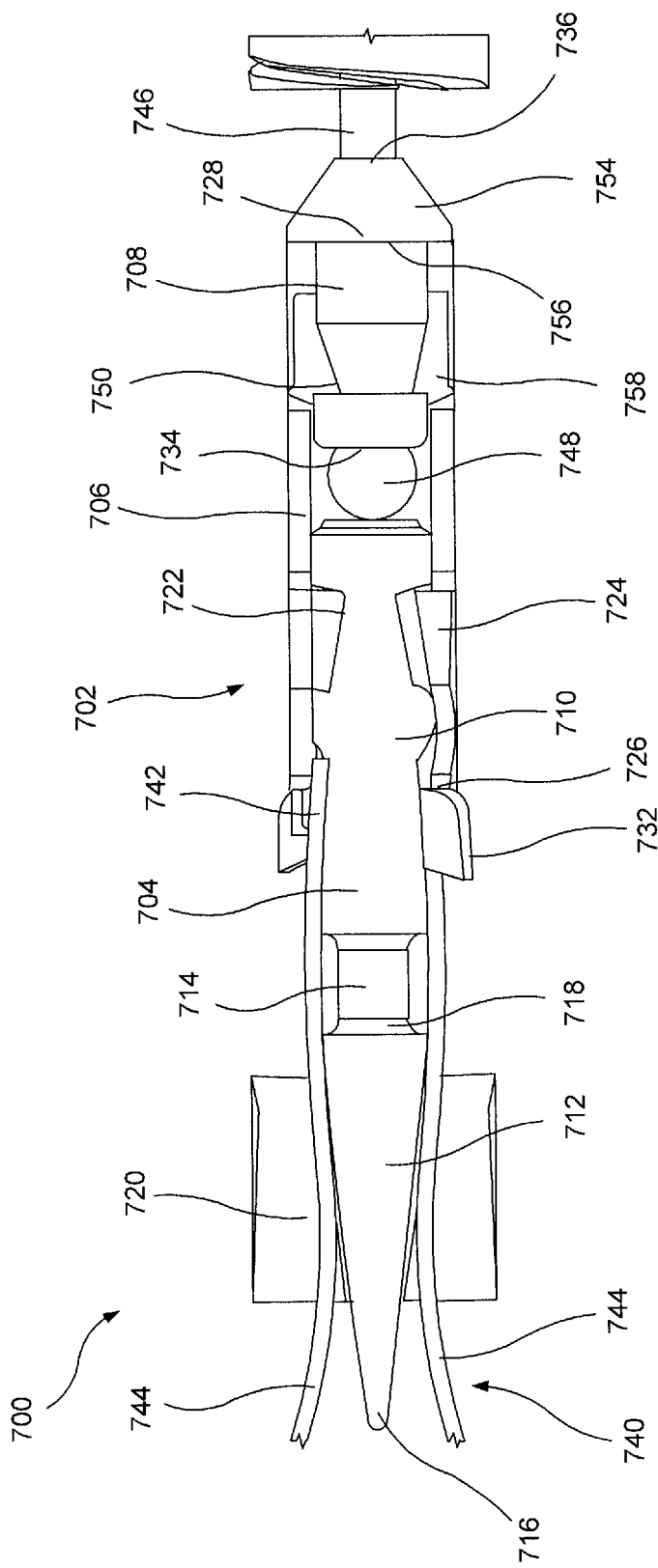
FIG. 18 shows a side view of a device according to a seventh embodiment of the invention.
Figure 19:
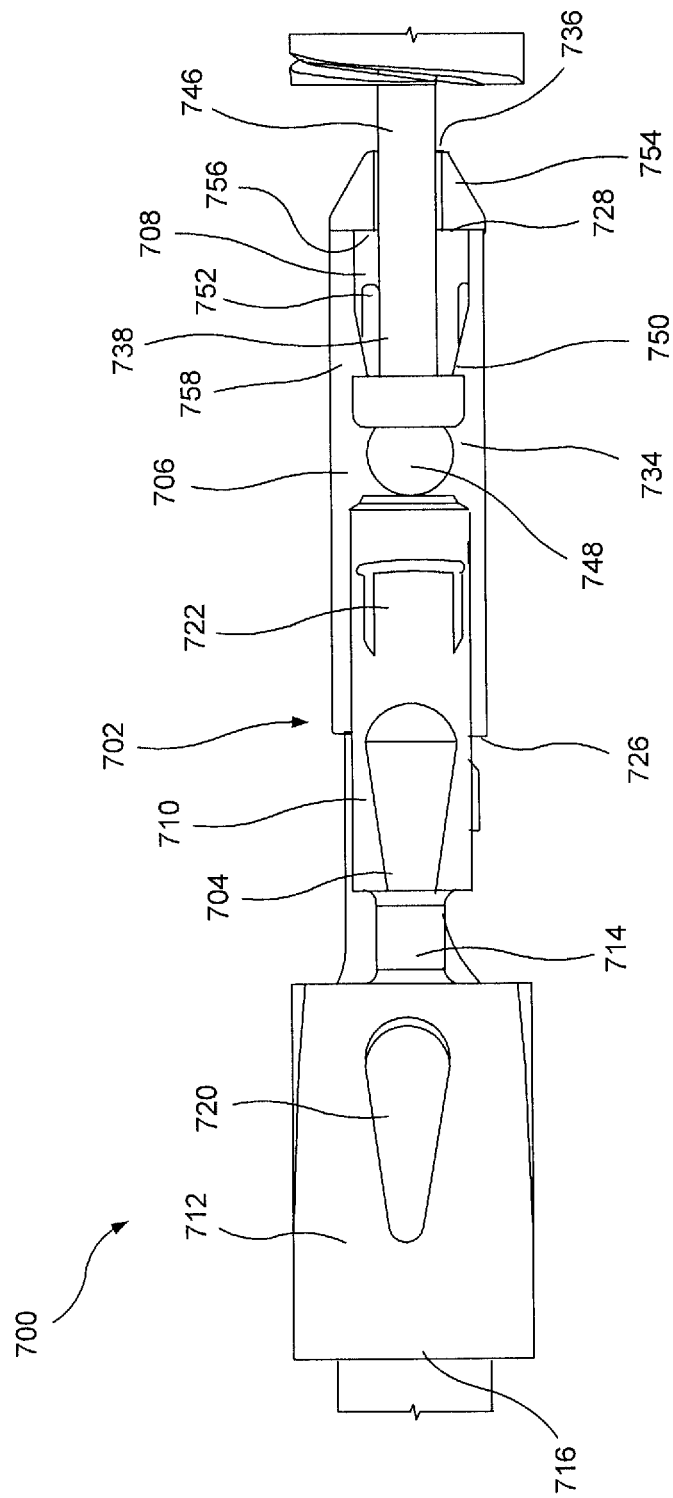
FIG. 19 shows a side view of the device of FIG. 18 rotated relative to FIG. 18 about a longitudinal axis of the device.

According to another embodiment of the invention as shown in FIGS. 18 and 19, a device 700 comprises a core member including first, second and third components 704, 706, 708, respectively. The first component 704 includes proximal and distal portions 710, 712, respectively, connected to one another via a frangible link 714 designed to fail when subjected to a load of at least a predetermined level. The distal portion 712 may be tapered such that it extends from a tapered distal tip 716 to a proximal end 718 connected to the proximal portion 710 via the frangible link 714. The distal portion 712 includes protrusions 720 positioned on opposite sides of the distal portion 712 for engaging proximal ends 742 of arms 744 of a clip 740. The proximal portion 710 includes an indented portion 722 (or two indented portions 722 in this case) for engaging a bent tab 724 of the second component 708. The second component 708 may be a hypotube with a lumen 730 extending therethrough from a distal end 726 to a proximal end 728. The distal end 726 includes constraint tabs 732 for securing proximal ends 742 of the clip 740. The bent tab 724, which may be bent during the manufacturing process, may be located proximally of the constraint tabs 732 to engage the indented portion 722 of the first component 704 when the first component 704 is slid through the lumen 730 of the second component 706.

The third component 708 may extend longitudinally from a distal end 734 to a proximal end 736 with a lumen 738 extending therethrough. The lumen 738 may be sized and shaped to accommodate a control wire 746, which may include a ball-tip 748 at a distal end thereof. The ball-tipped end 748 may be larger in diameter than a diameter of the control wire 746 and a diameter of the lumen 738 such that when the control wire 746 is passed through the lumen 738 from the distal end 734, the ball-tipped end 748 does not pass therethrough and abuts the distal end 734. The third component 706 may also include a distal portion 752 and a proximal portion 754. The distal portion 752 may have a diameter that is less than a diameter of the proximal portion 754 such that the distal portion 752 may fit within the lumen 746 while a distal end 756 of the proximal portion 754 abut the proximal end 728 of the second component 706. The distal portion 752 may include an indentation 750 for engaging a corresponding protrusion 758 on an inner surface of the second component 706. The indentation 750 may be formed radially around a portion of a length of the distal portion 752 while the protrusion 758 is formed correspondingly around an inner surface of the second component 706. However, it will be understood by those of skill in the art that the indentation 750 and the protrusion 758 may take any shape and/or form so long as the indentation 750 and the protrusion 758 correspond to and engage with one another. Thus, when the control wire 746 is drawn proximally, the core member 702 and all its components 704, 706 and 708 are all drawn proximally until a predetermined load is reached and the frangible link 714 is broken.

Figure 20:
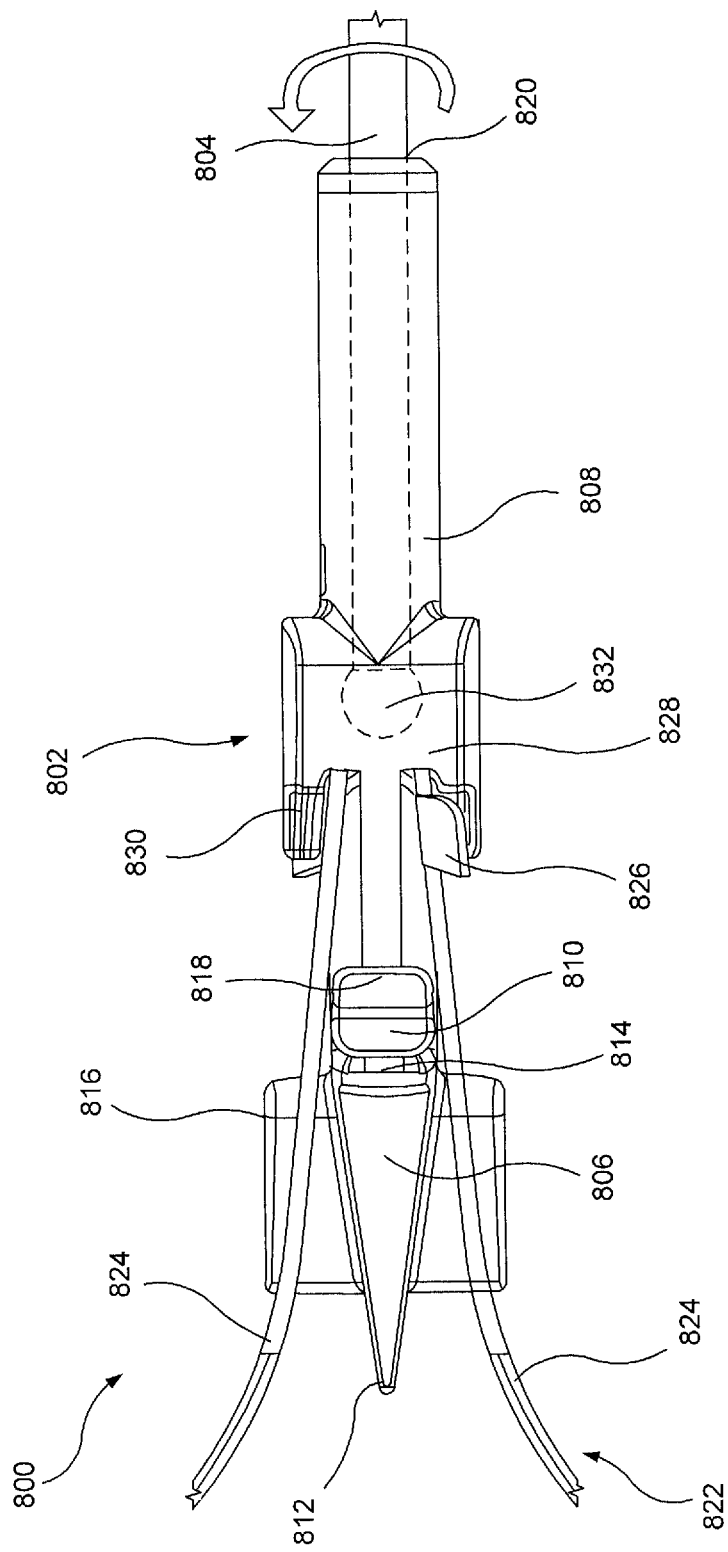
FIG. 20 shows a side view of a device according to an eighth embodiment of the invention.
Figure 21:
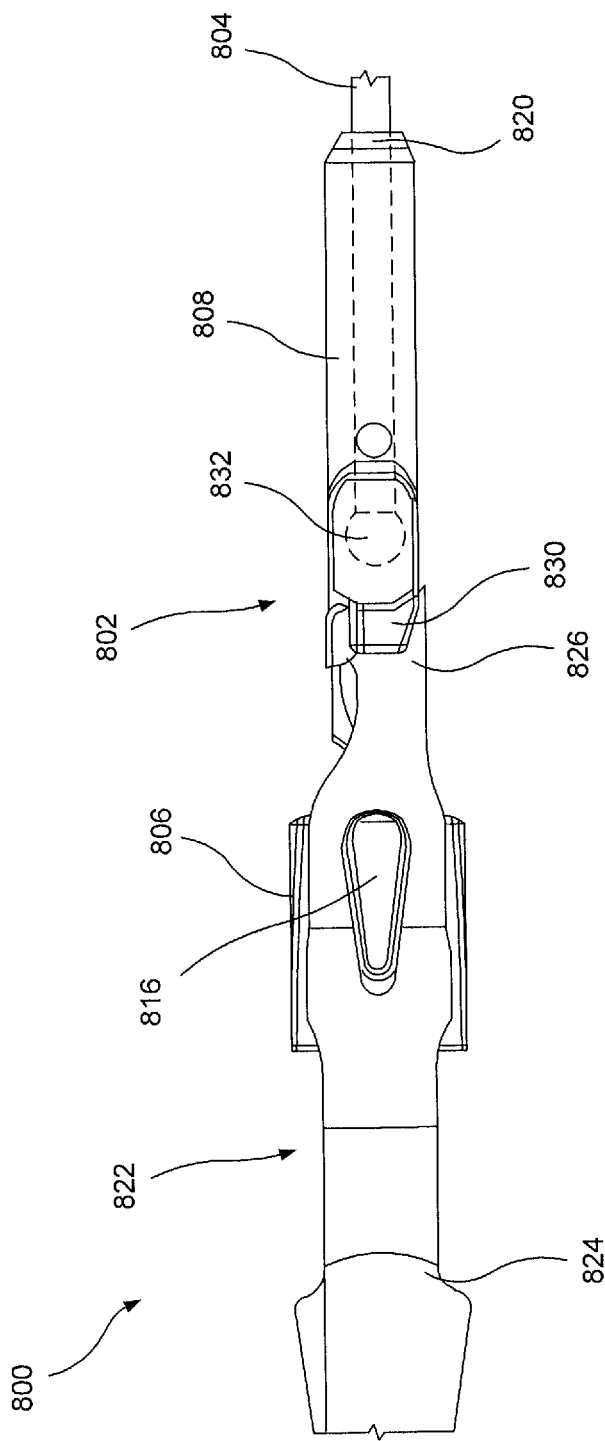
FIG. 21 shows a side view of the device of FIG. 20 rotated relative to FIG. 20 about a longitudinal axis of the device.

As shown in FIGS. 20 and 21, a device 800 according to another embodiment of the present invention, comprises a core member 802 extending over (e.g., overmolded on) a control wire 804. The core member 802 may be substantially similar to the core member 106 of the device 100 except that the core member 802 is overmolded onto the control wire 804. The core member 802 may be formed from a single piece including first and second portions 806, 808 connected to one another via a frangible link 810. The first portion 806 may be tapered such that it extends from a tapered tip 812 at a distal end thereof to a proximal end 814 connected to the second portion 808 via the frangible link 810. The first portion 806 further includes protrusions 816 formed on opposite sides of the first portion 806 for engaging arms 824 of a clip 822. The second portion 808 may be substantially longitudinal extending from a distal end 818, which connects to the first portion 806 via the frangible link 810, to a proximal end 820. The second portion 808 includes a constraining portion 828 along a portion of a length thereof between the distal end 818 and the proximal end 820. The constraining portion 828 may include constraining tabs 830 at a distal end thereof for securing proximal ends 826 of arms 824. It will be understood by those of skill in the art that the constraining portion 828 may have a diameter larger than that of the remaining portion of the second portion 808 such that the constraining tabs 830 may press the proximal end 826 of the arms 824 against the remaining portion of the second portion 808.

The core member 802 may be overmolded on the control wire 804 such that a distal end 832 of the control wire is positioned within the constraining portion 828. It will be understood by those of skill in the art that the core member 802 may be used to deploy the clip 822 in substantially the same manner as described above in regard to the device 100 or any of the other embodiments of the invention. However, since the core member 802 is overmolded on the control wire 804, a user may apply a torque to the control wire 804, rotating it about a longitudinal axis of the device 800, thereby loosening a bond between the material of the core member 802 and that of the control wire 804 so that the control wire 804 may be rotated relative to the core member 802. Even when loosened, the control wire 804 is secure within the core member 802 such that the control wire 804 may be used to draw the core member 802 proximally.

It will be understood by those of skill in the art that all of the clipping devices described above and all of their components may be formed of a variety of different materials such as, for example, plastic, metals, superelastic materials, shape memory materials, resilient shapes, etc. Each of the components may be formed via any manufacturing method such as, for example, machining, molding, lithographing, etching, etc.

It will be apparent to those skilled in the art that the various modifications may be made in the present invention, without departing from the spirit or scope of the invention. Thus, it is intended that the present invention cover modifications and variations of this invention provided that they come within the scope of the appended claims and their equivalents.

What is claimed is:

1. A device, comprising:
 a clip including first and second arms biased toward an open configuration in which the first and second arms are separated from one another;
 a unitary core member including first and second portions connected to one another via a frangible link designed to fail when subject to a predetermined load, the first portion including a first protrusion engaging a cut-out in the first arm;
 a capsule slidably housing the core member and a proximal portion of the clip such that when the clip is drawn proximally into the capsule the clip arms are urged toward one another to a closed configuration; and
 a bushing coupled to a proximal end of the capsule via cantilever arms engaging windows of the capsule when supported by an outer surface of the second portion of the core member.

2. The device of claim 1, wherein the second portion includes a first constraining tab substantially aligned with the first protrusion along a length of the core member to engage a proximal end of the first arm.

3. The device of claim 2, wherein the second portion includes a second constraining tab engaging a proximal end of the second arm.

4. The device of claim 1, wherein the first portion includes a second protrusion engaging a cut-out in the second arm.

5. The device of claim 1, wherein the second portion includes a lumen extending through the second portion, the lumen being sized to accommodate a tensioning member.

6. The device of claim 5, wherein the tensioning member includes an enlarged distal end, a diameter of the enlarged distal end is larger than a diameter of the lumen so that, when a proximal portion of the tensioning member is drawn proximally into the lumen, the enlarged distal end abuts a distal opening of the lumen.

7. The device of claim 1, wherein the capsule includes a tab at a distal end thereof separating the first and the second arms of the clip and preventing the core member from sliding distally beyond the tab.

8. The device of claim 1, wherein the first portion of the core member includes a tapered tip at a distal end thereof.

9. The device of claim 1, wherein the first protrusion and the cut-out are substantially tear-shaped.

10. The device of claim 1, wherein the cantilever arms are biased toward a longitudinal axis of the device so that, when the frangible link is severed and the second portion is retracted out of contact with the cantilever arms, the cantilever arms retract radially inward out of engagement with the windows in the capsule disengaging the capsule and the bushing from one another.

11. The device of claim 1, wherein the second portion includes a first element coupled to a second element, the second element extending from a distal end including constraint tabs to a proximal end, a lumen extending therethrough from the distal end to the proximal end and including a shoulder separating a distal, increased diameter portion of the lumen from a proximal reduced diameter portion thereof, the device further including a tensioning member extending through the lumen with an enlarged distal end of the tensioning member engaging the shoulder.

12. The device of claim 11, wherein the first element is overmolded onto the second element after the tensioning member has been inserted therethrough and further wherein the constraint tabs engage proximal ends of the first and second arms by securing the proximal ends against a surface of the first element.

13. The device of claim 12, wherein a third element is overmolded and welded to the second element within the first element such that the first element retains a load greater than a predetermined load.

14. The device of claim 1, wherein the second portion includes first and second clamshell elements which, when in an attached configuration, encase a distal element connected to the first portion via the frangible link.

15. The device of claim 1, wherein the frangible link comprises a snap mechanism including mating elements engaging one another with a proximal end of the first portion being received within a distal end of the second portion.

16. The device of claim 1, further comprising a tensioning member molded into a distal end of the second portion that is connected to the first portion.

17. The device of claim 1, wherein the second portion includes first, second and third components, the first component being connected to the first portion via the frangible link and receivable within a distal end of the second component, the third component including a lumen extending therethrough and a shoulder at a distal end thereof, the device further including a tensioning member extending through the lumen, the third component being received within a proximal end of the second component such that the an enlarged distal end of the tensioning member abuts a proximal end of the first component.

18. The device of claim 17, wherein bends on an inner surface of the second component lock the first and third components within the second component.

19. The device of claim 1, wherein the first and second portions are integrally formed with the core member being overmolded directly onto a tensioning member extending therethrough.

20. The device of claim 1, wherein the frangible link comprises a weld configured to fracture when subject to a predetermined load.

21. A device, comprising:
a clip including first and second arms biased toward an open, tissue receiving configuration;
a unitary core member including first and second portions connected to one another via a frangible link designed to fail when subject to a predetermined load, the first portion including a first protrusion engaging a cut-out in the first arm, the first portion further including a second protrusion engaging a cut-out in the second arm;
a capsule slidably housing the core member and a proximal portion of the clip such that when the clip is drawn proximally into the capsule the first and second arms are urged toward one another to a closed configuration; and
a bushing coupled to a proximal end of the capsule via cantilever arms engaging windows of the capsule when supported by an outer surface of the second portion.

22. The device of claim 21, wherein the capsule is locked over the clip when the frangible link is severed to lock the arms in a closed configuration.

\* \* \* \* \*